United States Patent [19]

Saida et al.

[11] Patent Number: 5,530,139
[45] Date of Patent: Jun. 25, 1996

[54] CONDENSED HETEROCYCLIC COMPOUND WITH A SULFONIC ACID GROUP AND PROCESS FOR PRODUCING THE SAME

[75] Inventors: Yoshihiro Saida; Yoshiaki Ikenoue, both of Chiba; Reiko Ichikawa, Osaka, all of Japan

[73] Assignee: Showa Denko Kabushiki Kaisha, Tokyo, Japan

[21] Appl. No.: 251,266

[22] Filed: May 31, 1994

[30] Foreign Application Priority Data

May 31, 1993 [JP] Japan .................................. 5-129797
Apr. 20, 1994 [JP] Japan .................................. 6-081841

[51] Int. Cl.$^6$ .................. C07D 333/72; C07D 495/04; C07D 495/14; C07D 495/22
[52] U.S. Cl. .................. 549/3; 549/41; 549/42; 549/44; 549/51; 546/10; 546/41; 546/47; 546/62; 546/80; 544/225; 544/350; 544/278; 544/235; 544/345
[58] Field of Search .................. 549/51, 44, 42, 549/41, 3

[56] References Cited

FOREIGN PATENT DOCUMENTS 2258832 10/1990 Japan .
2258833 10/1990 Japan .

OTHER PUBLICATIONS

Davies, D. T. *Aromatic Heterocyclic Chemistry* (Oxford University Press, Oxford, 1992), p. 38.

*J. Org. Chem.*, vol. 56, No. 21, 1991 6024–6026 (1991). A New Route to 1,3–Disubstituted Benzo[c] thiophenes, Yoshihiro Okuda, M. V. Lakshmikantham, and Michael P. Cava month of publication not provided.

*Organic Functional Group Preparations*, ed. by S. R. Sandler and W. Karo published by Academic Press, New York, 1968; 506–511 month of publication not provided.

Primary Examiner—Cecilia Tsang
Assistant Examiner—King Lit Wong
Attorney, Agent, or Firm—Sughrue, Mion, Zinn, Macpeak & Seas

[57] ABSTRACT

A condensed heterocyclic compound having a structure represented by formula (I):

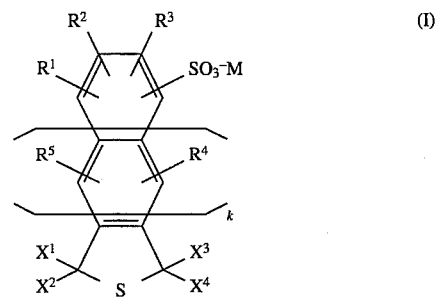

wherein the substituents are as defined in the specification herein.

3 Claims, No Drawings

CONDENSED HETEROCYCLIC COMPOUND WITH A SULFONIC ACID GROUP AND PROCESS FOR PRODUCING THE SAME

FIELD OF THE INVENTION

The present invention relates to a novel compound useful as various intermediates and to a process for producing the same. More specifically, the present invention relates to a compound useful as a reaction raw material or a reaction intermediate in many fields of the chemical industry, and in addition, suitable as a monomer for an electroconductive polymer useful as an electrode, a sensor, an electronic display element, a nonlinear optic element, a photoelectric conversion element, or an antistatic agent, which involves severe processability requirements in the field of electric and electronic industries, as well as useful as various electroconductive or optical materials.

BACKGROUND OF THE INVENTION

Many reports have hitherto been made on condensed heterocyclic compounds, for example, on 1,3-dihydrobenzo[c]thiophene, 1,3-dihydronaphtho[2,3-c]thiophene, and their analogous derivatives (for example, in A. R. Katrizky and A. J. Boulton, *Advances in Heterocyclic Chemistry*, vol. 10, Academic Press, New York (1969)). A generally known example of the synthesis method concerned is a method to produce 1,3-dihydrobenzo[c]thiophene or 1,3-dihydronaphtho[2,3-c]thiophene, comprising the ring-closure of o-dibromoxylene, o-dichloroxylene, 2,3-bisbromo-methylnaphthalene, or the substitution products thereof using sodium sulfide (see *Recl. Trav. Chim. Pays-Bas*, vol. 87(10), p. 1006, 1968). Further, reports have also been made on the ring-closure reaction of the above-described dihalogeno compounds using lithium sulfide and the reduction reaction of thiophthalic acid anhydride.

However, 1,3-dihydrobenzo[c]thiophene,1,3-dihydronaphtho[2,3-c]thiophene, and their analogous derivatives are deficient because they are highly reactive and cannot be stored in air at room temperature (about 20°–30° C.) for a long period of time (an oxidative dehydrogenation reaction being spontaneously and incompletely induced to give rise to blackening as a result of undesired oligomerization or polymerization).

Accordingly, for incorporating a substituent into an aromatic ring, a desired substituent is previously incorporated into a precursor, then the above-described dihalogeno compound is produced, and the ring-closure reaction is carried out according to the above-described method and the like to produce a 1,3-dihydrobenzo[c]thiophene or 1,3-dihydronaphtho[2,3-c]thiophene derivative with a substituent (see JP-A-2-308847, the term "JP-A" as used herein means an unexamined published Japanese patent application").

EP291269-A1 describes a 1,3-dihydrobenzo[c]thiophene derivative having a sulfonamide group as an example of a compound with a substituent, but the publication does not disclose any specific production process thereof. Among condensed heterocyclic compounds with a sulfonic acid group, JP-A-2-252727 describes a compound having a benzo[c]thiophene (or alternatively called isothianaphthene) in which condensed benzene ring is conjugated with carbon atoms in the 1- and 3-positions, but the publication does not disclose any specific production process thereof nor the properties thereof. Further, there is no report of a condensed heterocyclic compound with both a sulfonic acid group and a dihydrothiophene structure, for example, a sulfonic acid-substituted compound of 1,3-dihydrobenzo[c]thiophene, 1,3-dihydronaphtho[2,3-c]thiophene, or a derivative thereof.

SUMMARY OF THE INVENTION

The present invention provides a stable condensed heterocyclic compound capable of being stably stored in air at room temperature for a long period of time and a process for producing the same. The condensed heterocyclic compound with a sulfonic acid group of the present invention is a compound which can exist in air at room temperature for a long period of time and is highly useful and expected to be used not only as a monomer of an electroconductive polymer material but also as a reaction raw material or a reaction intermediate in other industrial fields (for example, agricultural, medical, food industries, etc.).

An object of the present invention is to provide a sulfonic acid-substituted condensed heterocyclic compound which is stable at room temperature by incorporating a sulfonic acid group, for example, a sulfonic acid-substituted compound having a structure analogous to a condensed heterocyclic structure of 1,3-dihydrobenzo[c]thiophene, 1,3-dihydronaphtho[2,3-c]thiophene, and a derivative thereof.

As a result of an extensive investigation on a monomer useful, in particular, for producing a π-electron conjugated electroconductive polymer material, it has been found that a compound having excellent stability can be obtained by directly sulfonating a heterocyclic compound, for example, 1,3-dihydrobenzo[c]thiophene, 1,3-dihydronaphtho[2,3-c]thiophene, or various substituted derivatives thereof and as a result a process for producing a novel sulfonic acid-containing condensed heterocyclic compound of the present invention has been developed.

That is, the present invention provides a condensed heterocyclic compound having a structure represented by formula (I):

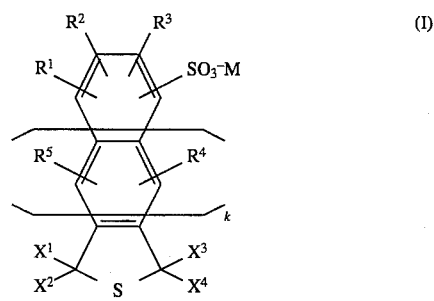

wherein substituents $R^1$, $R^2$, $R^3$, $R^4$ and $R^5$ each independently represents a monovalent moiety selected from the group consisting of a hydrogen atom, a linear or branched, saturated or unsaturated alkyl, alkoxy or alkyl ester group having from 1 to 20 carbon atoms, an $SO_3^-M$ group, a halogen atom, a nitro group, a cyano group, a primary, secondary, or tertiary amino group, a trihalomethyl group, a phenyl group, and a substituted phenyl group, with the proviso that the group consisting of substituents $R^1$, $R^2$, $R^3$, $R^4$ and $R^5$ does not include two or more $SO_3^-M$ groups simultaneously, the hydrocarbon chain of $R^1$, $R^2$, $R^3$, $R^4$ or $R^5$ may combine with each other at any optional position to form at least one divalent chain which forms, together with two carbon atoms of the substituted ring, at least one 3- to 7-membered saturated or unsaturated hydrocarbon ring, and the alkyl group, the alkoxy group, or the alkyl ester group of $R^1$, $R^2$, $R^3$, $R^4$ and $R^5$, or the cyclic hydrocarbon chain formed therefrom may optionally contain a moiety such as a carbonyl, an ether, an ester, an amide, a sulfide, a sulfinyl, a sulfonyl, and an imino group; M represents $H^+$, an alkali metal ion such as $Na^+$, $Li^+$, and $K^+$, or an unsubstituted or alkylo or aryl-substituted cation of a Group Vb element such as $NH_4^+$, $NH(CH_3)_3^+$, $N(CH_3)_4^+$, $NH(C_2H_5)_3^+$, $N(C_6H_5)_4^+$, $PH_4^+$, $P(CH_3)_4^+$, $P(C_6H_5)_4^+$, $AsH_4^+$, $As(CH_3)_4^+$, and $As(C_6H_5)_4^+$; k represents an integer of from 0 to 3 indicating the number of condensed rings enclosed by a dihydrothiophene ring and a benzene ring having substituents $R^1$, $R^2$, and $R^3$, and the condensed ring in the formula may optionally contain a nitrogen atom or an N-oxide group; and the substituents $X^1$, $X^2$, $X^3$ and $X^4$ each independently represents a hydrogen atom, a halogen atom, a linear or branched, saturated or unsaturated alkyl group having from 1 to 5 carbon atoms, a phenyl group or a substituted phenyl group and the alkyl group of $X^1$, $X^2$, $X^3$ or $X^4$ may optionally contain a moiety such as a carbonyl, an ether, an ester, an amide, a sulfide, a sulfinyl, a sulfonyl, and an imino group.

Further, the present invention provides a novel benzo[c]thiophene derivative having the structure represented by formula (II):

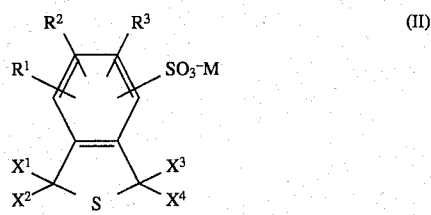

(II)

wherein $R^1$, $R^2$, $R^3$, M, $X^1$, $X^2$, $X^3$ and $X^4$ each has the same meaning as in formula (I) and a novel naphtho[2,3-c]thiophene derivative having the structure represented by formula (III):

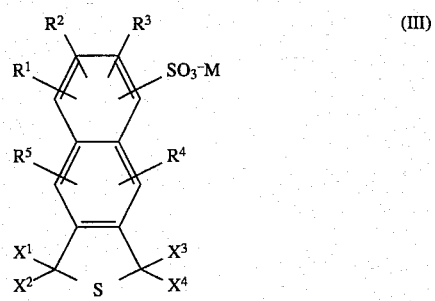

(III)

wherein $R^1$, $R^2$, $R^3$, $R^4$, $R^5$, M, $X^1$, $X^2$, $X^3$ and $X^4$ each has the same meaning as in formula (I).

Furthermore, the present invention provides a process for producing a condensed heterocyclic compound having a structure represented by the abovedescribed formula (I) comprising reacting a sulfonating reagent with a compound having a structure represented by formula (IV):

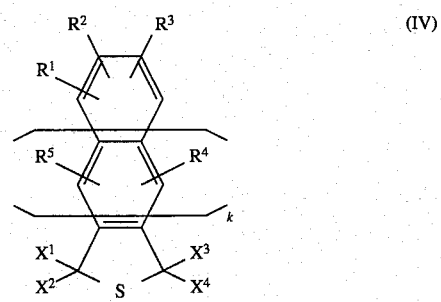

(IV)

wherein substituents $R^1$, $R^2$, $R^3$, $R^4$ and $R^5$ each independently represents a monovalent moiety selected from the group consisting of a hydrogen atom, a linear or branched, saturated or unsaturated alkyl, alkoxy or alkyl ester group having from 1 to 20 carbon atoms, a halogen atom, a nitro group, a cyano group, a primary, secondary, or tertiary amino group, a trihalomethyl group, a phenyl group, and a substituted phenyl group, with the proviso that the hydrocarbon chain of $R^1$, $R^2$, $R^3$, $R^4$ or $R^5$ may combine with each other at any optional position to form at least one divalent chain which forms, together with two carbon atoms of the substituted ring, at least one 3- to 7-membered saturated or unsaturated hydrocarbon ring, and the alkyl group, the alkoxy group, and the alkyl ester group of $R^1$, $R^2$, $R^3$, $R^4$, and $R^5$, or the cyclic hydrocarbon chain formed therefrom may optionally contain a moiety such as a carbonyl, an ether, an ester, an amide, a sulfide, a sulfinyl, a sulfonyl and an imino group; k represents an integer of from 0 to 3 indicating the number of condensed rings enclosed by a dihydrothiophene ring and a benzene ring having substituents $R^1$, $R^2$, and $R^3$, and the condensed ring in the formula may optionally contain a nitrogen atom or an N-oxide group; and the substituents $X^1$, $X^2$, $X^3$ and $X^4$ each independently represents a hydrogen atom, a halogen atom, a linear or branched, saturated or unsaturated alkyl group having from 1 to 5 carbon atoms, a phenyl group or a substituted phenyl group, and the alkyl group of $X^1$, $X^2$, $X^3$ or $X^4$ may optionally contain a moiety such as a carbonyl, an ether, an ester, an amide, a sulfide, a sulfinyl, a sulfonyl, and an imino group.

DETAILED DESCRIPTION OF THE INVENTION

The present invention is now described in detail below.

The compounds having a dihydrothiophene ring and a condensed benzene ring are useful, in particular, as a monomer for a π-electron conjugated electroconductive polymer or its precursor, and among those, 1,3-dihydrobenzo[c]thiophene or 1,3-dihydronaphtho[2,3-c]thiophene provides poly(benzo[c]thiophene) (called polyisothianaphthene) or poly(naphtho[2,3-c]thiophene) (see JP-A-63-118323) through an oxidative polymerization reaction, respectively. In particular, poly(benzo[c]thiophene) has the lowest bandgap (1 eV) as a semiconductor and is of interest as an electroconductive polymer showing a high electroconductivity with a small amount of dopants.

Known examples of the π-electron conjugated electroconductive polymer are poly[2-(3-thienyl)ethanesulfonic acid] and poly[4-(3-thienyl)butanesulfonic acid] and these polymers are reported, in terms of their characteristics as having a sulfonic acid group, as being water-soluble and as self-doping polymers requiring no external dopant (see *Synthetic Metals*, vol. 20, p. 151, Elsevier Sequoia (1987)).

The compounds of the present invention are now described in detail.

Particularly useful examples of substituents $R^1$, $R^2$, $R^3$, $R^4$ and $R^5$ in the abovedescribed formula (I) include a hydrogen atom, a halogen atom, an $SO_3^-M$ group, a saturated alkyl group, an unsaturated alkyl group, a saturated alkoxy group, an unsaturated alkoxy group, a saturated alkyl ester group, and an unsaturated alkyl ester group. More specific examples of these substituents include halogen atoms such as a chlorine, bromine, fluorine and iodine atom, moieties such as methyl, ethyl, propyl, isopropyl, butyl, t-butyl, pentyl, hexyl, octyl, dodecyl, tetradecyl, methoxyethyl, ethoxyethyl, acetonyl, and phenacyl as the hydrocarbon of the alkyl group or the alkyl ester group, and moieties such as methoxy, (2-methoxy)ethoxy, ethoxy, propoxy, isopropoxy, hexyloxy, octyloxy, and dodecyloxy as the alkoxy group.

In addition to the above, examples of suitable substituents for $R^1$, $R^2$, $R^3$, $R^4$ and $R^5$ include an amino group such as methylamino, ethylamino, diphenylamino, and anilino, and a group such as trifluoromethyl, phenyl, tosyl, xylyl, chlorophenyl and acetamido.

Particularly useful examples of M in formula (I) include $H^+$, alkali metal ions such as $Na^+$, $Li^+$ and $K^+$, and ammonium ions such as $NH_4^+$, $NH(CH_3)_3^+$, $N(CH_3)_4^+$, $NH(C_2H_5)_3^+$ and $N(C_6H_5)_4^+$.

Particularly useful examples of the substituents $X^1$, $X^2$, $X^3$ and $X^4$ in formula (I) include a hydrogen atom, a halogen atom, an alkyl group and a phenyl group. More specific examples of substituents include halogen atoms such as chlorine, bromine and fluorine, and alkyl groups such as methyl and ethyl. Additional examples of $X^1$, $X^2$, $X^3$ and $X^4$ include a tosyl group, a carboxylic acid group and a carbamoyl group.

k in formula (I) represents an integer of from 0 to 3 indicating the number of condensed rings enclosed by a dihydrothiophene ring and a benzene ring having the substituents $R^1$, $R^2$ and $R^3$. The hydrocarbon chain of the substituent $R^1$, $R^2$, $R^3$, $R^4$ or $R^5$ may combine with each other at any optional position to form at least one divalent chain linked together such as unsubstituted or substituted methylene, unsubstituted or substituted ethylene, unsubstituted or substituted vinylene, unsubstituted or substituted trimethylene, unsubstituted or substituted propenylene, unsubstituted or substituted tetramethylene, unsubstituted or substituted butenylene, unsubstituted or substituted butadienylene, unsubstituted or substituted butynylene, unsubstituted or substituted pentamethylene, unsubstituted or substituted pentenylene, unsubstituted or substituted pentadienylene, unsubstituted or substituted pentynylene and unsubstituted or substituted dioxymethylene, which forms, together with two carbon atoms of the substituted ring, at least one 3- to 7-membered saturated or unsaturated hydrocarbon ring. The condensed ring may optionally contain a nitrogen atom or an N-oxide group. Suitable examples include thieno[3,4-b]quinoxaline and thieno[3,4-b]quinoxaline-4,9-dioxide.

Representative examples of fundamental skeletons of the condensed ring of the compound represented by formula (I) are set forth below, but the present invention should not be construed as being limited thereto.

(I-1) 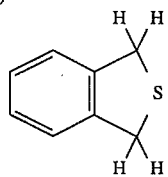 (I-2) 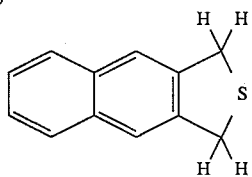

(I-3) 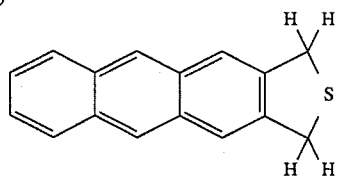

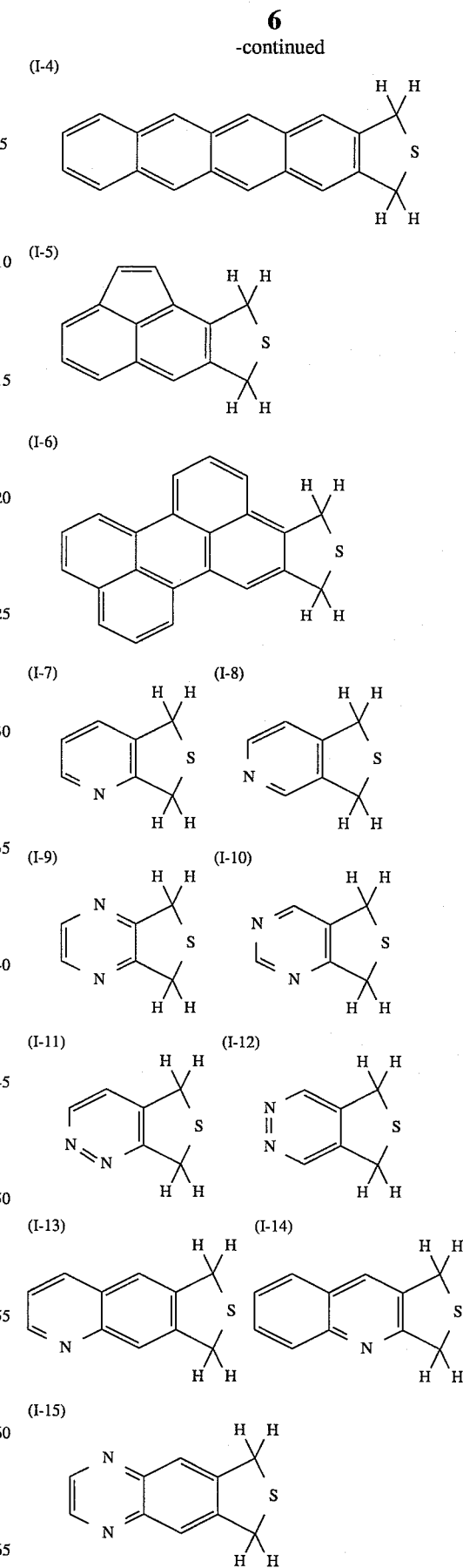

Specific examples of compounds represented by the formula (II) are set forth below, but the present invention should not be construed as being limited thereto.

(II-1) 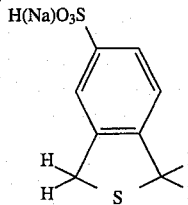

(II-2) 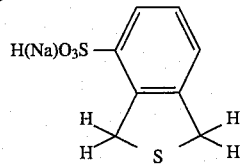

(II-3) 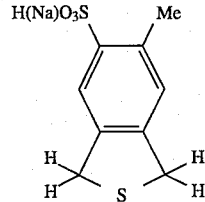

(II-4) 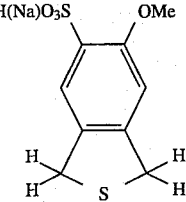

(II-5) 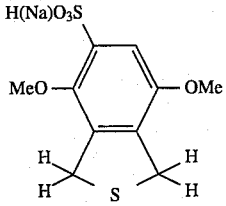

(II-6) 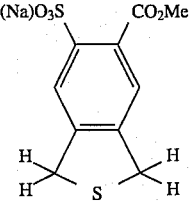

(II-7) 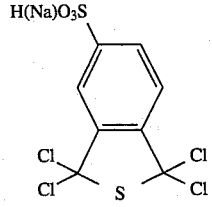

(II-8) 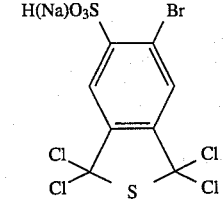

(II-9) 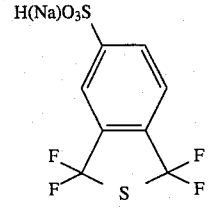

(II-10) 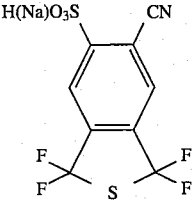

(II-11) 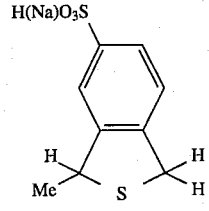

(II-12) 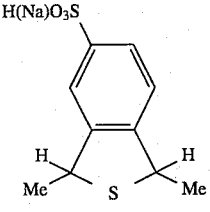

(II-13) 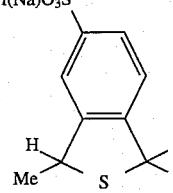

(II-14) 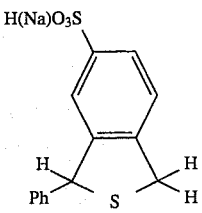

(II-15) 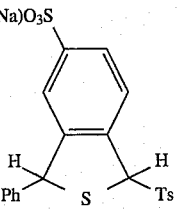

Specific examples of compounds represented by formula (III) are set forth below, but again the present invention should not be construed as being limited thereto.

(III-1) 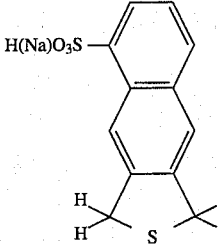

(III-2) 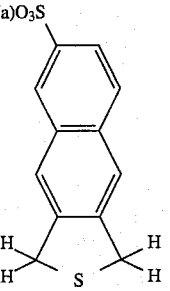

(III-3) 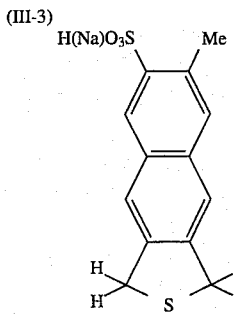

(III-4) 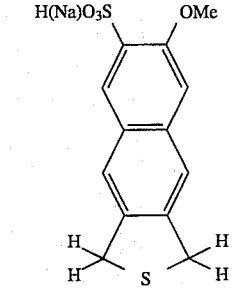

(III-5) 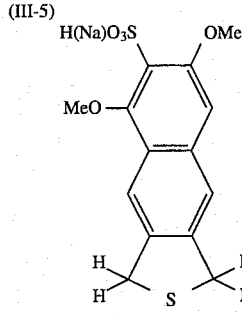

(III-6) 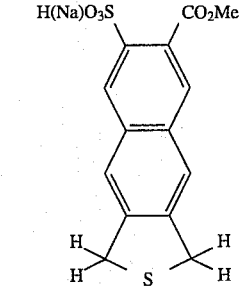

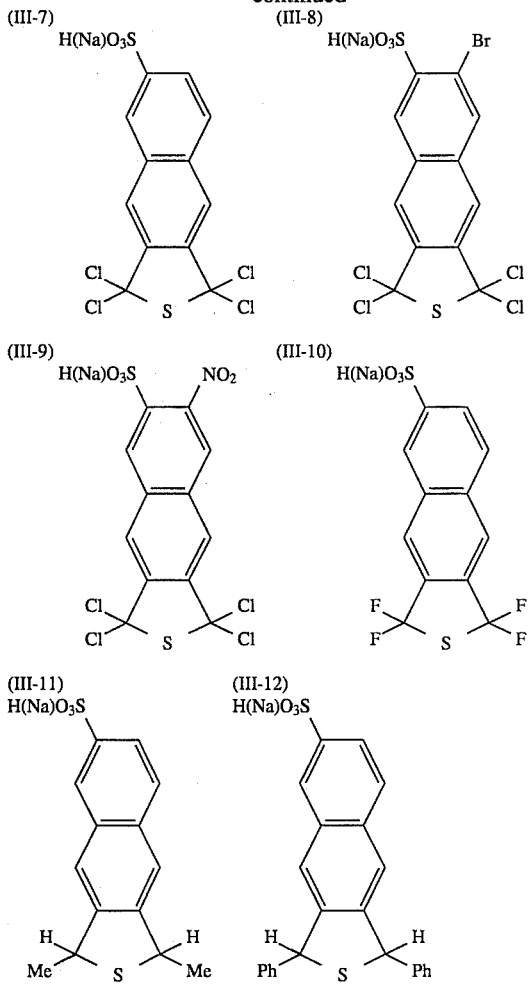

A process for producing compounds represented by formula (I) is described below.

The compound represented by formula (I) can be produced by reacting a sulfonating reagent with a compound having a structure represented by formula (IV);

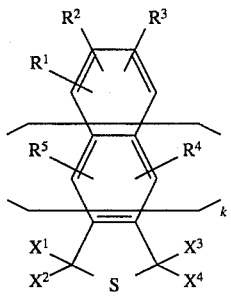

wherein substituents $R^1$, $R^2$, $R^3$, $R^4$ and $R^5$ each independently represents a monovalent moiety selected from the group consisting of a hydrogen atom, a linear or branched, saturated or unsaturated alkyl, alkoxy or alkyl ester group having from 1 to 20 carbon atoms, a halogen atom, a nitro group, a cyano group, a primary, secondary, or tertiary amino group, a trihalomethyl group, a phenyl group, and a substituted phenyl group, with the proviso that the hydrocarbon chain of $R^1$, $R^2$, $R^3$, $R^4$ or $R^5$ may combine with each other at any optional position to form at least one divalent chain which forms, together with two carbon atoms of the substituted ring, at least one 3- to 7-membered saturated or unsaturated hydrocarbon ring, and the alkyl group, the alkoxy group, and the alkyl ester group of $R^1$, $R^2$, $R^3$, $R^4$ and $R^5$, or the cyclic hydrocarbon chain formed therefrom may optionally contain a moiety such as a carbonyl, an ether, an ester, an amide, a sulfide, a sulfinyl, a sulfonyl, and an imino group; k represents an integer of from 0 to 3 indicating the number of condensed rings enclosed by a dihydrothiophene ring and a benzene ring with substituents $R^1$, $R^2$, and $R^3$, and the condensed ring in the formula may optionally contain a nitrogen atom or an N-oxide group; and the substituents $X^1$, $X^2$, $X^3$ and $X^4$ each independently represents a hydrogen atom, a halogen atom, a linear or branched, saturated or unsaturated alkyl group having from 1 to 5 carbon atoms, a phenyl group or a substituted phenyl group, and the alkyl group of $X^1$, $X^2$, $X^3$ or $X^4$ may optionally contain a moiety such as a carbonyl, an ether, an ester, an amide, a sulfide, a sulfinyl, a sulfonyl, and an imino group. Specifically, a sulfonation substitution reaction occurs in the compound represented by formula (IV) to result in a compound having the structure represented by formula (I).

In greater detail, an example is described using a compound represented by formula (II) in which k of formula (I) is 0 and $X^1$, $X^2$, $X^3$ and $X^4$ are each a hydrogen atom.

The compound which is a precursor of the compound represented by the structure of formula (II) and in which k of formula (IV) is 0 is already known, and the production, for example, of a compound wherein the substituents $X^1$, $X^2$, $X^3$ and $X^4$ are a hydrogen atom are described in *Recl. Trav. Chim. Pays-Bas,* vol. 87(10), p. 1006, 1968. Further, the compound wherein the substituents $X^1$, $X^2$, $X^3$ and $X^4$ all are Cl or F is described in *J. Gen. Chem. USSR,* vol. 36, p. 1421, 1966.

In the present invention, examples of the sulfonating reagent which can be used in the sulfonation substitution reaction generally include sulfuric acid, fuming sulfuric acid, sulfur trioxide, chlorosulfuric acid, fluorosulfuric acid, and amidosulfuric acid, and among them, fuming sulfuric acid and sulfur trioxide are preferred. A mixture of two or more sulfonating reagents may also be used if desired. The amount of the sulfonating reagent used will vary depending upon the kind of compound having a structure represented by formula (IV) or the sulfonating reagent used and therefore, cannot be defined specifically, but it is generally in the range preferably from an equimolar amount to a 20-fold molar amount, more preferably from a 1.1-fold to 5-fold molar amount, per mol of the compound represented by formula (IV).

Where a liquid sulfonating reagent such as sulfuric acid and fuming sulfuric acid is used as the sulfonating reagent, the sulfonating reagent acts as the solvent and therefore, the addition of a solvent is not necessarily required, but a reaction solvent may be used for controlling the reaction temperature or the reaction time if desired. The solvent used may be any solvent as long as the solvent dissolves the compound and the sulfonating reagent and does not inhibit the sulfonation substitution reaction. Specific examples thereof include water, sulfuric acid, fuming sulfuric acid, formic acid, acetic acid, propionic acid, acetic acid anhydride; an ether such as tetrahydrofuran, dioxane, and diethyl ether; a polar solvent such as dimethylformamide, acetonitrile, benzonitrile, N-methylpyrrolidone (NMP), and dimethylsulfoxide (DMSO); an ester such as ethyl acetate and butyl acetate; and a non-aromatic chlorinated solvent such as chloroform and methylene chloride. A mixture of these solvents may also be used if desired.

The concentration of the compound having the structure represented by formula (IV) for use in the production process for compounds of the present invention will vary depending upon the kind of the compound, the reaction scale or the solvent used, but it is generally in the range preferably from $10^{-3}$ to 10 mol/l, more preferably from $10^{-2}$ to 1 mol/l.

The reaction temperature will be dependent on the respective reaction methods and cannot be specifically set forth, but it is generally at a temperature range preferably from −80° C. to 80° C., more preferably from −30° C. to 50° C. The reaction time varies depending upon the reaction method, the reaction temperature, the reaction pressure or the structure of the compound and cannot be described absolutely, but usually, it is preferably from 0.01 to 240 hours, more preferably from 0.1 to 20 hours. The reaction pressure is preferably from $10^{-5}$ to 100 atm, more preferably from 1 to 10 atm, most preferably normal pressure.

In order to prevent production of by-products having a sulfone bond generated from the thus synthesized compound having a sulfo group of the present invention as a concomitant side reaction during the sulfonation reaction, known sulfone production inhibitors such as a fatty acid, an organic peroxide, an acid anhydride, pyridine, acetic acid or a ketone may be added in an amount of from 0.01 to 50 wt % as long as they do not inhibit the reaction.

The thus produced compound of the formula (I) can be used to produce various sulfonic acid derivatives according to conventional processes for producing a sulfonic acid compound (for example, a process described in *Shinjikken Kagaku Koza14, Synthesis and Reaction of Organic Compounds (III)*, edited by Chemical Society of Japan, Maruzen, pp. 1793–1809 (1978)) and can be used as a starting material or an intermediate for producing a sulfonic acid derivative, e.g., a halogenated sulfonyl compound, a sulfonic acid ester, a sulfonic acid anhydride, and a sulfonamide.

An additional use of the compound represented by formula (I) can be to produce a π-conjugated electroconductive polymer through an oxidative polymerization reaction.

As described above, the condensed heterocyclic compound having a sulfonic acid substituent of the present invention, specifically, 1,3-dihydrobenzo[c]thiophene-sulfonic acid (or its salt), 1,3-dihydronaphtho[2,3-c]thiophene-sulfonic acid (or its salt), or a derivative thereof, is useful as a raw material to produce various compounds and as a monomer of a π-conjugated electroconductive polymer, and is produced by the above-described production process.

The condensed heterocyclic compound with a sulfonic acid group according to the present invention has an electron-attracting sulfonic acid and therefore, is extremely stable in air and is a novel compound, useful as an intermediate compound in various uses. More specifically, the compound of the present invention is useful as an important reaction raw material or reaction intermediate in many industrial fields. In particular, the compound can be appropriately used as a monomer of a π-electron conjugated electroconductive polymer.

Further, according to the production process of the present invention, the above-described useful novel condensed heterocyclic compound can be easily produced.

The present invention is now described in greater detail by reference to the following Examples. However, the present invention should not be construed as being limited thereto. Unless otherwise indicated all parts, percents, ratios and the like are by weight.

EXAMPLE 1

Synthesis Example of Compound wherein in Formula (II), $R^1$, $R^2$, $R^3$, $X^1$, $X^2$, $X^3$ and $X^4$ Each is Hydrogen (H), and M is $Na^+$ 4 ml of fuming sulfuric acid (20% sulfur trioxide) was kept at 20° C. or lower and 1 g of 1,3-dihydrobenzo[c]thiophene, a known compound, was gradually added thereto with stirring. By allowing the mixture to stand, the temperature returned to room temperature and, on continuing the stirring for 4 hours, the reaction solution became brown.

The reaction mixture was dissolved in 150 ml of ice water, 20 g of sodium chloride was added thereto, followed by heating to dissolve it uniformly, to cause gradual salting out, and then separation was effected using a centrifuge. After removing the supernatant liquid, the residue was vacuum dried to provide 650 mg of sodium 1,3-dihydrobenzo[c]thiophene-5-sulfonate (gray powder).

IR ($cm^{-1}$): 3060, 2900, 2840, 1480, 1440, 1400, 1220, 1170, 1050

$^1H$ NMR ($D_2O$, ppm): 4.30(s), 7.46(d), 7.65(d), 7.73(s)

$^{13}C$ NMR ($D_2O$, ppm): 36.7, 36.8, 121.7, 124.1, 125.1, 141.1, 141.3, 144.0

Elemental Analysis (%):

|  | C | H | S | Na |
|---|---|---|---|---|
| Calcd. | 40.3 | 3.0 | 26.9 | 9.7 |
| Found | 39.5 | 3.5 | 26.1 | 9.2 |

EXAMPLE 2

Synthesis Example of Compound wherein in Formula (II), $R^1$, $R^2$ and $R^3$ Each is Hydrogen (H), M is $Na^+$, and $X^1$, $X^2$, $X^3$ and $X^4$ Each is Chlorine (Cl)

4 ml of fuming sulfuric acid (20% sulfur trioxide) was kept at 0° C. or lower and 1 g of 1,1,3,3-tetrachlorobenzo[c]thiophene, a known compound, was gradually added thereto with stirring. On allowing the mixture to stand, the temperature returned to room temperature, and, when the stirring was continued for 24 hours, the reaction solution became brown.

The reaction mixture was dissolved in 150 ml of ice water, 20 g of sodium chloride was added thereto, followed by heating to dissolve it uniformly, to cause gradual salting out, and then separation was effected using a centrifuge. After removing the supernatant liquid, the residue was vacuum dried to provide 450 mg of sodium 1,1,3,3-tetrachlorobenzo[c]thiophene-5-sulfonate (gray powder).

IR ($cm^{-1}$): 1230, 1180, 1050

$^1H$ NMR ($D_2O$, ppm): 7.46(d), 7.65(d), 7.73(s)

Elemental Analysis (%):

|  | C | H | S | Na | Cl |
|---|---|---|---|---|---|
| Calcd. | 25.6 | 0.8 | 17.1 | 6.1 | 37.7 |
| Found | 24.9 | 1.1 | 16.7 | 6.0 | 36.8 |

EXAMPLE 3

Synthesis Example of Compound wherein in Formula (III), $R^1$, $R^2$, $R^3$, $R^4$, $R^5$, $X^1$, $X^2$, $X^3$ and $X^4$ Each is Hydrogen (H), M is $Na^+$ 2 ml of fuming sulfuric acid (20% sulfur trioxide) was kept at 20° C. or lower and 0.5 g of 1,3-dihydronaphtho[2,3-c]thiophene, a known compound, was gradually added thereto with stirring. By allowing the mixture to stand, the temperature returned to room temperature, and, when the stirring was continued for 4 hours, the reaction solution became green.

The reaction mixture was dissolved in 100 ml of ice water, 20 g of sodium chloride was added thereto, followed by heating to dissolve it uniformly, to cause gradual salting out, and then separation was effected using a centrifuge. After removing the supernatant liquid, the residue was vacuum dried to provide 350 mg of sodium 1,3-dihydronaphtho[2,3-c]thiophene-6-sulfonate (gray powder).

IR (cm$^{-1}$): 3060, 2900, 2850, 1480, 1400, 1220, 1180, 1050

$^1$H NMR (D$_2$O, ppm): 4.30(s), 7.3(d)-7.9(m)

Elemental Analysis (%):

|  | C | H | S | Na |
|---|---|---|---|---|
| Calcd. | 50.0 | 3.2 | 22.2 | 8.0 |
| Found | 48.5 | 3.4 | 21.6 | 7.7 |

EXAMPLE 4

The results of stability testing under general environmental conditions are shown in Table 1 below.

TABLE 1

Evaluation after Long-Term Storage

| Compound | Results of Stability Test*$^1$ | Remarks |
|---|---|---|
| Sodium 1,3-dihydrobenzo[c]-thiophene-5-sulfonate | No change in color for 6 months*$^2$ | Present invention |
| Sodium 1,1,3,3-tetrachloro-benzo[c]thiophene-5-sulfonate | No change in color for 6 months*$^2$ | Present invention |
| Sodium 1,3-dihydronaphtho-[2,3-c]thiophene-6-sulfonate | No change in color for 6 months*$^2$ | Present invention |
| 1,3-Dihydrobenzo[c]thiophene mp 23° C. | The oil completely turned bluish gray. | Comparative example |
| 1,3-Dihydronaphtho[2,3-c]-thiophene | The crystals turned bluish black gray. | Comparative example |

*$^1$Left to stand under conditions of 60% RH (relative humidity) and 20° C. in air.
*$^2$No chemical change (evaluation by NMR analysis)

While the invention has been described in detail and with reference to specific embodiments thereof, it will be apparent to one skilled in the art that various changes and modifications can be made therein without departing from the spirit and scope thereof.

What is claimed is:

1. A condensed heterocyclic compound having a structure represented by formula (I):

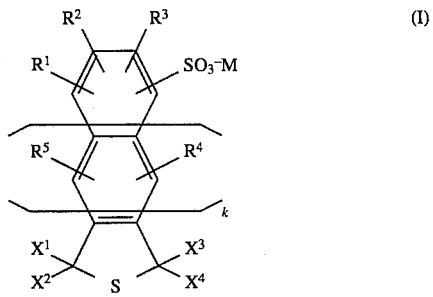

(I)

wherein substituents R$^1$, R$^2$, R$^3$, R$^4$ and R$^5$ each independently represent a monovalent moiety selected from the group consisting of a hydrogen atom, a linear or branched, saturated or unsaturated alkyl, alkoxy, or alkoxycarbonyl group having from 1 to 20 carbon atoms, an SO$_3^-$M group, a halogen atom, a nitro group, a cyano group, a primary, secondary, or tertiary amino group, a trihalomethyl group, a phenyl group, and a substituted phenyl group, with the proviso that the group consisting of substituents R$^1$, R$^2$, R$^3$, R$^4$ and R$^5$ does not include two or more SO$_3^-$M groups simultaneously, wherein the hydrocarbon chain of R$^1$, R$^2$, R$^3$, R$^4$ or R$^5$ may combine with each other at any optional position to form at least one divalent chain which forms, together with two carbon atoms of the substituted ring, at least one 6-membered saturated or unsaturated hydrocarbon ring or at least one 5- to 7-membered ortho-fused saturated or unsaturated hydrocarbon ring, and wherein the alkyl group, the alkoxy group, and the alkoxycarbonyl group of R$^1$, R$^2$, R$^3$, R$^4$ and R$^5$, or the cyclic hydrocarbon chain formed therefrom may optionally contain a moiety selected from the group consisting of a carbonyl, an ether, an ester, an amide, a sulfide, a sulfinyl, a sulfonyl and an imino group; M represents H$^+$, an alkali metal ion or an unsubstituted or alkyl- or aryl-substituted cation of a Group Vb element; k represents an integer of from 0 to 3 indicating the number of condensed rings enclosed by a dihydrothiophene ring and a benzene ring having substituents R$^1$, R$^2$, and R$^3$, and the substituents X$^1$, X$^2$, X$^3$ and X$^4$ each independently represent a hydrogen atom, a halogen atom, a linear or branched, saturated or unsaturated alkyl group having from 1 to 5 carbon atoms, a phenyl group or a substituted phenyl group and the alkyl group of X$^1$, X$^2$, X$^3$ or X$^4$ may optionally contain a moiety selected from the group consisting of a carbonyl, an ether, an ester, an amide, a sulfide, a sulfinyl, a sulfonyl, and an imino group.

2. A condensed heterocyclic compound as claimed in claim 1, wherein k of formula (I) is 0, comprising a benzo[c]thiophene derivative having a structure represented by formula (II);

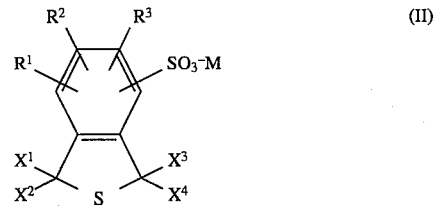

(II)

wherein R$^1$, R$^2$, R$^3$, M, X$^1$, X$^2$, X$^3$ and X$^4$ each has the same meaning as in formula (I).

3. A condensed heterocyclic compound as claimed in claim 1, wherein k of formula (I) is 1, comprising a naphtho[2,3-c]thiophene derivative having a structure represented by formula (III);

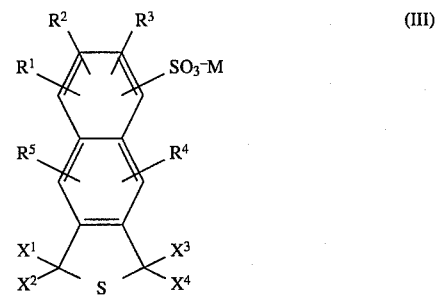

(III)

wherein R$^1$, R$^2$, R$^3$, R$^4$, R$^5$, M, X$^1$, X$^2$, X$^3$ and X$^4$ each has the same meaning as in formula (I).

* * * * *